US00PP12933P2

(12) United States Plant Patent
Zylstra

(10) Patent No.: US PP12,933 P2
(45) Date of Patent: Sep. 10, 2002

(54) *CUPRESSUS SEMPERVIRENS* 'MONSHEL'

(75) Inventor: Doug Zylstra, Santa Barbara, CA (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 09/696,660

(22) Filed: Oct. 26, 2000

(51) Int. Cl.[7] ..... A01H 5/00

(52) U.S. Cl. ..... Plt./213

(58) Field of Search ..... Plt./213

*Primary Examiner*—Bruce R. Campell
*Assistant Examiner*—Susan B. McCormick

(57) ABSTRACT

A new and distinct selection of *Cupressus sempervirens* (Italian Cypress) characterized by its unique combination of smaller, more dense ascending branchlets and finely textured and more green foliage which produces a more compact, tighter and smaller growth habit.

2 Drawing Sheets

BACKGROUND OF THE INVENTION

This invention relates to a new and distinct selection of *Cupressus sempervirens* Linneus, native to southern Europe and western Asia which is a member of the Cypress family. *Cupressus sempervirens* cv. 'Monshel' was a sport from a *Cupressus sempervirens* (non-patented) that I discovered in my Santa Barbara Nursery at 5297 Shoreline Drive, Santa Barbara, Calif. around October 1990. This discovery was not the result of a breeding program.

*Cupressus sempervirens* 'Monshel' has been asexually reproduced by vegetative cutting since October 1991 at Monrovia Nursery Company, 18331 East Foothill Boulevard, Azusa, Calif. Had this sport not been discovered and propagated, it may have been lost to mankind. It is unlikely the particular select and favorable attributes of this plant could be conveyed to progeny through sexual reproduction in the next generation, particularly as neither flower or fruit have been observed to date. However, through extensive propagation through vegetative cuttings it has been established that the novel exceptional characteristics of this plant are stable and reliably passed on to clonal specimens through asexual reproduction.

SUMMARY OF INVENTION

*Cupressus sempervirens* cv. 'Monshel' has fine textured foliage along with an unusually small stature, producing a diminutive effect of a plant, which normally has a stature of up to 25 meters tall. Typically, *Cupressus sempervirens* branchlets are not in a single plane resulting in a plant with depth and openness in growth habit. My selection has this typical characteristic of branchlets not in a single plane; however, the smaller leaf size does not make the angled branches as prominent as in the typical *Cupressus sempervirens* and my selection exhibits a tighter and more dense foliage habit.

My selection also is smaller in overall size. An eight-year-old specimen, the oldest known, has achieved a height of 2.1 meters and a width of 34 cm. *Cupressus sempervirens* and *Cupressus sempervirens* 'Glauca' at eight years of age are both approximately 75 percent larger with a height of 3.5 meters and a width of 50 centimeters.

The most widely available cultivar in the nursery industry is *Cupressus sempervirens* 'Glauca' (not patented). The foliage color on this cultivar is more grey blue, Green Group138B with a mix of Greyed-Green Group194B. Another cultivar *Cupressus sempervirens* 'Totem' (not patented) is also more grey, Green Group138B with tones of Greyed Green Group 191B. My selection has a much more green color (see botanical description) than either of these two selections.

My selection, 'Monshel', has tolerated cold temperatures from a low of 0° F., which is equivalent to a USDA hardiness zone 8, without exhibiting any damage.

BRIEF DESCRIPTION OF ILLUSTRATION

Figure 1:
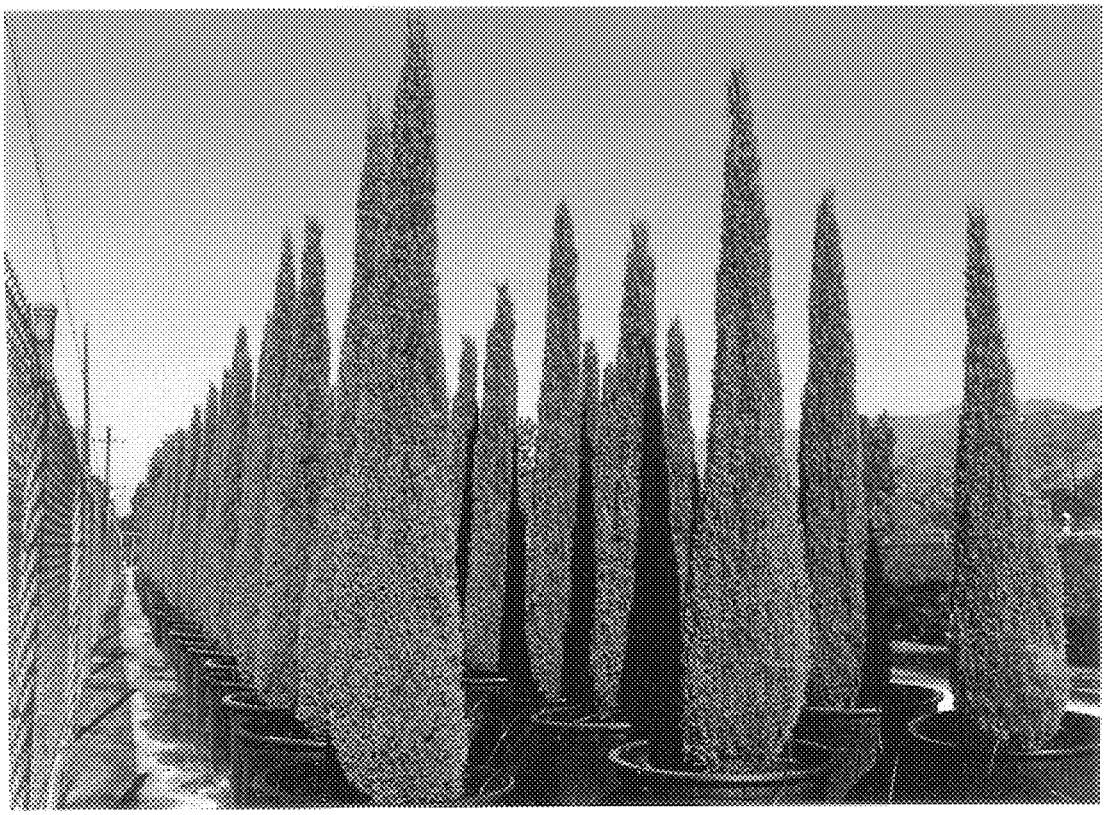

The accompanying photographs illustrate the present invention as follows:

FIG. 1 shows eight year old specimens of my selection in containers which display an extremely dense habit and size of approximately two meters tall and thirty to thirty four centimeters in width.

Figure 2:
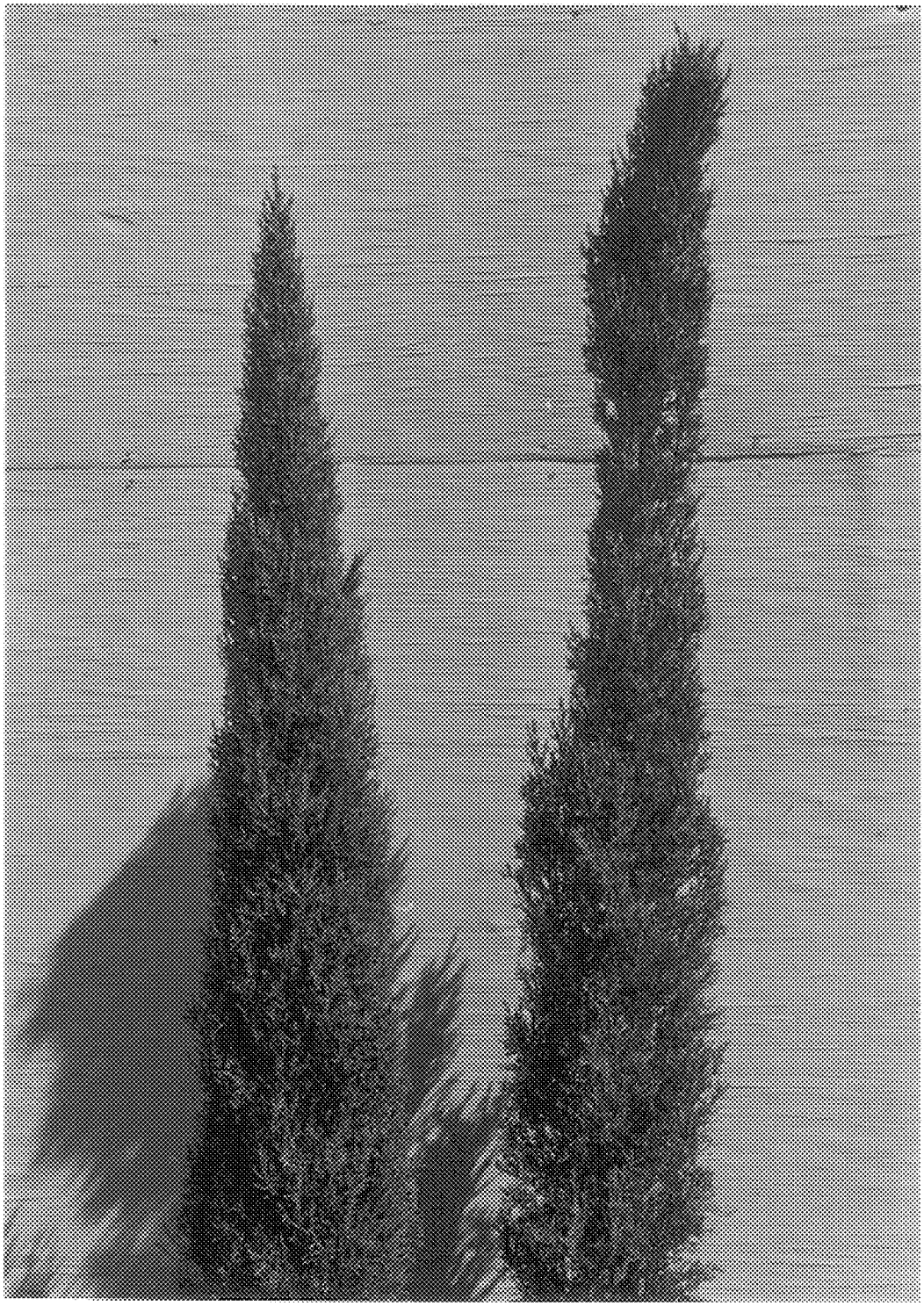

FIG. 2 compares the dense, uniform and tight growth habit of my selection 'Monshel' on the left with 'Glauca' on the right.

BOTANICAL DESCRIPTION

Below is a detailed description of *Cupressus sempervirens* cultivar 'Monshel', the color terminology is from The Royal Horticultural Society Colour Charts. Measurements are based on plants grown in southern California.

Overall habit: Upright, columnar, evergreen conifer.
Overall size: After eight years two meters tall and thirty-four centimeters at the widest portion— maximum height estimated at six meters.
Branchlets: Terete, slightly four (4) angled.
Trunk diameter: Of eight year old plant, measured two to three centimeters above soil level ranging from three to four centimeters. *Cupressus sempervirens* 'Glauca' at the same age ranges in diameter from 2.5 to 3 centimeters.
Foliage:
*Arrangement.*—Decussate.
*Shape.*—Scale-like, densely imbricate, appressed, ovate, obtuse at apex, longitudinal furrows on the dorsal side.

*Length.*—2 mm.

*Color.*—Green Group 137B and 137C.

Branch density: Density ranging from forty to fifty percent denser than *Cupressus sempervirens* 'Glauca'.

Branch color:

*Juvenile.*—Greyed-orange group 173B.

*Mature primary.*—Grey group 201D.

Branch angle: Thirty degree angle. *Cupressus sempervirens* 'Glauca' slightly wider to 45 degree angle.

Fragrance: Resinous odor to foliage.

Cone: Not observed.

Seeds: Not observed.

Disease resistance: Similar to *Cupressus sempervirens* 'Glauca'.

I claim:

1. A new and distinct *Cupressus sempervirens* plant named 'Monshel', substantially as illustrated and described herein.

* * * * *